United States Patent
Hancock et al.

(10) Patent No.: US 11,090,116 B2
(45) Date of Patent: Aug. 17, 2021

(54) ELECTROSURGICAL APPARATUS AND METHOD FOR PROMOTING HAEMOSTASIS IN BIOLOGICAL TISSUE

(71) Applicant: CREO MEDICAL LIMITED, Chepstow (GB)

(72) Inventors: Christopher Paul Hancock, Bath (GB); Francis Amoah, Chepstow (GB); Martin Jarman, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 446 days.

(21) Appl. No.: 16/091,497

(22) PCT Filed: May 19, 2017

(86) PCT No.: PCT/EP2017/062198
§ 371 (c)(1),
(2) Date: Oct. 4, 2018

(87) PCT Pub. No.: WO2017/202737
PCT Pub. Date: Nov. 30, 2017

(65) Prior Publication Data
US 2019/0125442 A1    May 2, 2019

(30) Foreign Application Priority Data
May 23, 2016 (GB) ..................... 1609012

(51) Int. Cl.
*A61B 18/10* (2006.01)
*A61B 18/12* (2006.01)
(Continued)

(52) U.S. Cl.
CPC .......... *A61B 18/1815* (2013.01); *A61B 1/015* (2013.01); *A61B 18/1206* (2013.01);
(Continued)

(58) Field of Classification Search
CPC ........ A61B 2018/00642; A61B 1/3132; A61B 1/2676; A61B 18/14; A61B 1/015;
(Continued)

(56) References Cited

U.S. PATENT DOCUMENTS 7,070,595 B2 * 7/2006 Ormsby ............. A61B 18/1492
606/33
2003/0158551 A1 * 8/2003 Paton ................. A61B 18/1206
606/51

(Continued)

FOREIGN PATENT DOCUMENTS

CN    201912225 U    8/2011
EP    1 810 627 A1    7/2007
(Continued)

OTHER PUBLICATIONS

British Search Report of related British Patent Application No. GB1609012.8 dated Dec. 1, 2016.
(Continued)

*Primary Examiner* — Linda C Dvorak
*Assistant Examiner* — Lindsay Regan Lancaster
(74) *Attorney, Agent, or Firm* — Arent Fox LLP

(57) ABSTRACT

An electrosurgical waveform having both radiofrequency (RF) energy and microwave energy components that is arranged to perform efficient haemostasis in biological tissue. The waveform comprises a first portion primarily of RF electromagnetic energy, and a second portion primarily of microwave electromagnetic energy that follows the first portion. The second portion further comprises a plurality of RF pulses, wherein the first portion transitions to the second portion when either a duration of the first portion meets or exceeds a predetermined duration threshold, or an impedance determined during the first portion meets or exceeds a predetermined threshold. The waveform is arranged to
(Continued)

deliver energy rapidly so that haemostasis can occur in a short time frame in a situation where the maximum available power is limited, or to avoid undesirable thermal damage to the biological tissue.

28 Claims, 3 Drawing Sheets

(51) Int. Cl.
| | |
|---|---|
| *A61B 18/18* | (2006.01) |
| *A61B 18/14* | (2006.01) |
| *A61N 5/04* | (2006.01) |
| *A61B 1/015* | (2006.01) |
| *A61B 18/08* | (2006.01) |
| *A61B 17/00* | (2006.01) |
| *A61B 18/00* | (2006.01) |
| *A61B 1/313* | (2006.01) |
| *A61B 1/267* | (2006.01) |
| *A61B 1/07* | (2006.01) |
| *A61B 1/00* | (2006.01) |
| *A61B 1/005* | (2006.01) |
| *A61B 1/06* | (2006.01) |
| *A61B 1/273* | (2006.01) |

(52) U.S. Cl.
CPC .......... *A61B 18/14* (2013.01); *A61B 18/1492* (2013.01); *A61N 5/04* (2013.01); *A61B 1/0052* (2013.01); *A61B 1/0057* (2013.01); *A61B 1/00195* (2013.01); *A61B 1/0684* (2013.01); *A61B 1/07* (2013.01); *A61B 1/2676* (2013.01); *A61B 1/2736* (2013.01); *A61B 1/3132* (2013.01); *A61B 2017/00115* (2013.01); *A61B 2017/00141* (2013.01); *A61B 2017/00176* (2013.01); *A61B 2018/00083* (2013.01); *A61B 2018/00494* (2013.01); *A61B 2018/00595* (2013.01); *A61B 2018/00642* (2013.01); *A61B 2018/00654* (2013.01); *A61B 2018/00678* (2013.01); *A61B 2018/00708* (2013.01); *A61B 2018/00779* (2013.01); *A61B 2018/00803* (2013.01); *A61B 2018/00827* (2013.01); *A61B 2018/00875* (2013.01); *A61B 2018/00886* (2013.01); *A61B 2018/00892* (2013.01); *A61B 2018/00982* (2013.01); *A61B 2018/00994* (2013.01); *A61B 2018/126* (2013.01); *A61B 2018/183* (2013.01); *A61B 2018/1823* (2013.01); *A61B 2018/1861* (2013.01)

(58) Field of Classification Search
CPC ... A61B 1/0684; A61B 1/0052; A61B 1/2736; A61B 2017/00115; A61B 18/1492; A61B 1/00195; A61B 1/0057; A61B 2017/00141; A61B 2018/00708; A61B 2018/00779; A61B 2018/183; A61B 2018/128; A61B 2018/00803; A61B 2018/00982; A61B 2018/126; A61B 2018/1823; A61B 2018/1861; A61B 2017/00176; A61B 2018/00494; A61B 18/1206; A61B 2018/00678; A61B 2018/00827; A61B 2018/00994; A61B 18/1815; A61B 2018/00875; A61B 2018/00886; A61B 2018/00892; A61B 18/1442; A61B 2018/00922; A61B 2018/0063; A61B 1/07; A61B 2018/00083; A61B 2018/00595; A61B 2018/00654; A61N 5/04

See application file for complete search history.

(56) References Cited

U.S. PATENT DOCUMENTS

| | | | |
|---|---|---|---|
| 2011/0071514 A1 | 3/2011 | Shin et al. | |
| 2014/0350548 A1* | 11/2014 | Schall | ................ A61B 18/1206 606/40 |
| 2015/0112324 A1* | 4/2015 | Cybulski | .............. A61B 18/042 606/34 |

FOREIGN PATENT DOCUMENTS

| | | | | |
|---|---|---|---|---|
| GB | 2486343 A | * | 6/2012 | ......... A61B 18/1815 |
| GB | 2487288 A | | 7/2012 | |
| WO | WO 2015/087051 A1 | | 6/2015 | |

OTHER PUBLICATIONS

International Search Report of related International Patent Application No. PCT/EP2017/062198 dated Jul. 31, 2017.

Written Opinion of related International Patent Application No. PCT/EP2017/062198 dated Jul. 31, 2017.

* cited by examiner

ELECTROSURGICAL APPARATUS AND METHOD FOR PROMOTING HAEMOSTASIS IN BIOLOGICAL TISSUE

CROSS-REFERENCE TO RELATED APPLICATIONS

This application is a National Stage Entry of International Patent Application No. PCT/EP2017/062198, filed May 19, 2017, which claims priority to Great Britain Application No. 1809012.8, filed May 23, 2016. The disclosures of the priority applications are incorporated in their entirety herein by reference.

FIELD OF THE INVENTION

The invention relates to an electrosurgical apparatus for coagulating biological tissue. In particular, it relates to a composite radiofrequency (RF) and microwave energy waveform for delivery from an electrosurgical generator to a bipolar electrode configuration at a distal end of an electrosurgical instrument. The composite radiofrequency (RF) and microwave energy waveform is arranged to promote effective haemostasis in biological tissue through the efficient delivery of heat energy.

BACKGROUND TO THE INVENTION

Surgical resection is a means of removing sections of organs from within the human or animal body. Such organs may be highly vascular. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood free cutting. For endoscopic procedures, it is also undesirable for a bleed to occur and not to be dealt with as soon as quickly as possible, or in an expedient manner, since the blood flow may obscure the operator's vision, which may lead to the procedure needing to be terminated and another method used instead, e.g. open surgery.

Electrosurgical generators are pervasive throughout hospital operating theatres, for use in open and laparoscopic procedures, and are also increasingly present in endoscopy suites. In endoscopic procedures the electrosurgical accessory is typically inserted through a lumen inside an endoscope. Considered against the equivalent access channel for laparoscopic surgery, such a lumen is comparatively narrow in bore and greater in length. In the case of a bariatric patient the surgical accessory may have a length of 300 mm from handle to RF tip, whereas the equivalent distance in a laparoscopic case can be in excess of 2500 mm.

Instead of a sharp blade, it is known to use radiofrequency (RF) energy to cut biological tissue. The method of cutting using RF energy operates using the principle that as an electric current passes through a tissue matrix (aided by the ionic contents of the cells and the intercellular electrolytes), the impedance to the flow of electrons across the tissue generates heat. When an RF voltage is applied to the tissue matrix, enough heat is generated within the cells to vaporise the water content of the tissue. As a result of this increasing desiccation, particularly adjacent to the RF emitting region of the instrument which has the highest current density of the entire current path through tissue, the tissue adjacent to the cut pole of the instrument loses direct contact with the blade. The applied voltage is then appears almost entirely across this void which ionises as a result, forming a plasma, which has a very high volume resistivity compared to tissue. This differentiation is important as it focusses the applied energy to the plasma that completed the electrical circuit between the cut pole of the instrument and the tissue. Any volatile material entering the plasma slowly enough is vaporised and the perception is therefore of a tissue dissecting plasma.

GB 2 486 343 discloses a control system for an electrosurgical apparatus which delivers both RF and microwave energy to treat biological tissue. The energy delivery profile of both RF energy and microwave energy delivered to a probe is set based on sampled voltage and current information of RF energy conveyed to the probe and sampled forward and reflected power information for the microwave energy conveyed to and from the probe.

FIG. 3 shows a schematic diagram of an electrosurgical apparatus 400 as set out in GB 2 486 343. The apparatus comprises a RF channel and a microwave channel. The RF channel contains components for generating and controlling an RF frequency electromagnetic signal at a power level suitable for treating (e.g. cutting or desiccating) biological tissue. The microwave channel contains components for generating and controlling a microwave frequency electromagnetic signal at a power level suitable for treating (e.g. coagulating or ablating) biological tissue.

The microwave channel has a microwave frequency source 402 followed by a power splitter 424 (e.g. a 3 dB power splitter), which divides the signal from the source 402 into two branches. One branch from the power splitter 424 forms a microwave channel, which has a power control module comprising a variable attenuator 404 controlled by controller 406 via control signal $V_{10}$ and a signal modulator 408 controlled by controller 406 via control signal $V_{11}$, and an amplifier module comprising drive amplifier 410 and power amplifier 412 for generating forward microwave EM radiation for delivery from a probe 420 at a power level suitable for treatment. After the amplifier module, the microwave channel continues with a microwave signal coupling module (which forms part of a microwave signal detector) comprising a circulator 416 connected to deliver microwave EM energy from the source to the probe along a path between its first and second ports, a forward coupler 414 at the first port of the circulator 416, and a reflected coupler 418 at the third port of the circulator 416. After passing through the reflected coupler, the microwave EM energy from the third port is absorbed in a power dump load 422. The microwave signal coupling module also includes a switch 415 operated by the controller 406 via control signal $V_{12}$ for connecting either the forward coupled signal or the reflected coupled signal to a heterodyne receiver for detection The other branch from the power splitter 424 forms a measurement channel. The measurement channel bypasses the amplifying line-up on the microwave channel, and hence is arranged to deliver a low power signal from the probe. In this embodiment, a primary channel selection switch 426 controlled by the controller 406 via control signal $V_{13}$ is operable to select a signal from either the microwave channel or the measurement channel to deliver to the probe. A high band pass filter 427 is connected between the primary channel selection switch 426 and the probe 420 to protect the microwave signal generator from low frequency RF signals.

The measurement channel includes components arranged to detect the phase and magnitude of power reflected from the probe, which may yield information about the material e.g. biological tissue present at the distal end of the probe.

The measurement channel comprises a circulator 428 connected to deliver microwave EM energy from the source 402 to the probe along a path between its first and second ports. A reflected signal returned from the probe is directed into the third port of the circulator 428. The circulator 428 is used to provide isolation between the forward signal and the reflected signal to facilitate accurate measurement. However, as the circulator does not provide complete isolation between its first and third ports, i.e. some of the forward signal may break through to the third port and interfere with the reflected signal, a carrier cancellation circuit is used that injects a portion of the forward signal (from forward coupler 430) back into the signal coming out of the third port (via injection coupler 432). The carrier cancellation circuit include a phase adjustor 434 to ensure that the injected portion is 180° out of phase with any signal that breaks through into the third port from the first port in order to cancel it out. The carrier cancellation circuit also include a signal attenuator 436 to ensure that the magnitude of the injected portion is the same as any breakthrough signal.

To compensate for any drift in the forward signal, a forward coupler 438 is provided on the measurement channel. The coupled output of the forward coupler 438 and the reflected signal from the third port of the circulator 428 are connected to respective input terminal of a switch 440, which is operated by the controller 406 via control signal $V_{14}$ to connect either the coupled forward signal or the reflected signal to a heterodyne receiver for detection.

The output of the switch 440 (i.e. the output from the measurement channel) and the output of the switch 415 (i.e. the output from the microwave channel) are connect to a respective input terminal of a secondary channel selection switch 442, which is operable by the controller 406 via control signal $V_{15}$ in conjunction with the primary channel selection switch to ensure that the output of the measurement channel is connected to the heterodyne receiver when the measurement channel is supplying energy to the probe and that the output of the microwave channel is connected to the heterodyne receiver when the microwave channel is supplying energy to the probe.

The heterodyne receiver is used to extract the phase and magnitude information from the signal output by the secondary channel selection switch 442. A single heterodyne receiver is shown in this system, but a double heterodyne receiver (containing two local oscillators and mixers) to mix the source frequency down twice before the signal enters the controller may be used if necessary. The heterodyne receiver comprises a local oscillator 444 and a mixer 448 for mixing down the signal output by the secondary channel selection switch 442. The frequency of the local oscillator signal is selected so that the output from the mixer 448 is at an intermediate frequency suitable to be received in the controller 406. Band pass filters 446, 450 are provided to protect the local oscillator 444 and the controller 406 from the high frequency microwave signals.

The controller 406 receives the output of the heterodyne receiver and determines (e.g. extracts) from it information indicative of phase and magnitude of the forward and/or reflected signals on the microwave or measurement channel. This information can be used to control the delivery of high power microwave EM radiation on the microwave channel or high power RF EM radiation on the RF channel. A user may interact with the controller 406 via a user interface 452, as discussed above.

The RF channel shown in FIG. 3 comprises an RF frequency source 454 connected to a gate driver 456 that is controlled by the controller 406 via control signal $V_{16}$. The gate driver 456 supplies an operation signal for an RF amplifier 458, which is a half-bridge arrangement. The drain voltage of the half-bridge arrangement is controllable via a variable DC supply 460. An output transformer 462 transfers the generated RF signal on to a line for delivery to the probe 420. A low pass, band pass, band stop or notch filter 464 is connected on that line to protect the RF signal generator from high frequency microwave signals.

A current transformer 466 is connected on the RF channel to measure the current delivered to the tissue load. A potential divider 468 (which may be tapped off the output transformer) is used to measure the voltage. The output signals from the potential divider 468 and current transformer 466 (i.e. voltage outputs indicative of voltage and current) are connected directly to the controller 406 after conditioning by respective buffer amplifiers 470, 472 and voltage clamping Zener diodes 474, 476, 478, 480 (shown as signals B and C in FIG. 3).

To derive phase information, the voltage and current signals (B and C) are also connected to a phase comparator 482 (e.g. an EXOR gate) whose output voltage is integrated by RC circuit 484 to produce a voltage output (shown as A in FIG. 3) that is proportional to the phase difference between the voltage and current waveforms. This voltage output (signal A) is connected directly to the controller 406.

The microwave/measurement channel and RF channel are connected to a signal combiner 114, which conveys both types of signal separately or simultaneously along cable assembly 116 to the probe 420, from which it is delivered (e.g. radiated) into the biological tissue of a patient.

A waveguide isolator (not shown) may be provided at the junction between the microwave channel and signal combiner. The waveguide isolator may be configured to perform three functions: (i) permit the passage of very high microwave power (e.g. greater than 10 W); (ii) block the passage of RF power; and (iii) provide a high withstanding voltage (e.g. greater than 10 kV). A capacitive structure (also known as a DC break) may also be provided at (e.g. within) or adjacent the waveguide isolator. The purpose of the capacitive structure is to reduce capacitive coupling across the isolation barrier.

SUMMARY OF THE INVENTION

At its most general, the present invention provides a waveform having both radiofrequency (RF) energy and microwave energy components that is arranged to perform efficient haemostasis in biological tissue. In particular, the waveform is arranged to deliver energy rapidly so that haemostasis can occur in a short time frame (e.g. equal to or less than 10 seconds, preferably equal to or less than 3 seconds) in situation where the maximum available power is limited, e.g. due to limitations in the power delivery capability of the device being used, or to avoid undesirable thermal damage to the biological tissue, e.g. desiccation or charring.

Thus, according to one aspect of the invention there is provided an electrosurgical apparatus comprising: an electrosurgical generator arranged to generate radiofrequency (RF) electromagnetic energy and a microwave electromagnetic energy; an electrosurgical instrument having a distal tip assembly for delivering RF electromagnetic energy and microwave electromagnetic energy into biological tissue; and a feed cable connected to deliver the RF electromagnetic energy and the microwave electromagnetic energy from the electrosurgical generator to the bipolar electrosurgical instrument, wherein the electrosurgical generator is arranged to detect a voltage and a current associated with the delivered RF electromagnetic energy, and wherein the generator is operable to: determine an impedance from the detected voltage and current; deliver the RF electromagnetic energy and the microwave electromagnetic energy in a composite waveform for promoting haemostasis in biological tissue, the composite waveform comprising: a first portion comprising primarily RF electromagnetic energy, and a second portion following the first portion, the second portion comprising primarily microwave electromagnetic energy, wherein the second portion further comprises a plurality of RF pulses, wherein the first portion transitions to the second portion when either: a duration of the first portion meets or exceeds a predetermined duration threshold, or an impedance determined by the generator during the first portion meets or exceeds a predetermined impedance threshold.

In this arrangement, the composite waveform delivers heat energy using an RF signal when the tissue in an state that is receptive to energy delivery by conduction. Energy delivery continues in this was until either the tissue changes state (e.g. becomes desiccated) in a manner that means RF energy is no longer effectively delivered or until a certain amount of heat energy has been delivered. At this point, the haemostasis treatment is continued using microwave energy, which is capable of delivering a direct heating effect deeper into the tissue but without the risk of charring at the tissue surface.

The predetermined duration threshold may be equal to or less than 1 second. In practice, the predetermined duration threshold may be set based on the anticipated energy delivered by the RF electromagnetic energy in the first portion. For example, it may be desirable to deliver 7 Joules of energy in the first portion. The voltage and current of the RF electromagnetic energy may be controlled to ensure that no more than the anticipated energy is delivered with the predetermined duration threshold.

The electrosurgical generator may be arranged to determine an initial impedance from the detected voltage and current associated with the RF electromagnetic energy delivered at the beginning of the first portion, and wherein the predetermined impedance threshold is a preset proportion of the initial impedance. This means it is not necessary to set an absolute value for the predetermined impedance threshold. It is now that as tissue is desiccated and become non-conductive, its impedance rises. By monitoring this rise, the transition to the second portion can occur before desiccation reaches a level at which there is a heightened risk of permanent tissue damage, e.g. due to charring. The preset proportion may be equal to or more than 1.25, i.e. the transition occurs when the determined impedance is 25% larger than the initial impedance.

The RF electromagnetic energy may be delivered as a continuous wave signal in the first portion. However, this is not essential. The RF energy may be delivered in a series of pulses, e.g. as described in WO2014/181078.

If a continuous wave signal is used for the RF electromagnetic energy, the signal may have an RMS voltage in the range 90-120 V. This can ensure that heating tails off with a rise in impedance in a manner that reduces the risk of accidental thermal damage.

Preferably the generator is arranged to output only RF energy in the first portion, i.e. no microwave electromagnetic energy is delivered in the first portion.

In the second portion, the microwave energy may be delivered as a continuous wave, e.g. having a preset (preferably user selectable) power level. The plurality of RF pulses may be supplied concurrently with the microwave electromagnetic energy, i.e. the RF electromagnetic energy and microwave electromagnetic energy may be supplied simultaneously for the duration of each RF pulse. Alternatively, delivery of the microwave electromagnetic energy may be paused during each RF pulse. Each of the plurality of RF pulses may be arranged to have a negligible thermal effect on the biological tissue. For example, the voltage and current and/or duration associated with the RF pulses may be limited in a manner that prevents thermal effect but enables an impedance measurement to be obtained.

The plurality of RF pulses may be supplied in a regular, e.g. periodic, manner.

The generator may be arranged to determine an impedance value from detected voltages and currents associated with each of the plurality of RF pulses delivered during the second portion. These determined impedance values can be used to calculate an amount of heat energy delivered by the electrosurgical instrument.

The generator may be operable to terminate the second portion when either: an amount of heat energy delivered by the electrosurgical instrument meets or exceeds a predetermined heat energy threshold, or a duration of the composite waveform meets or exceeds a predetermined total duration threshold. The predetermined total duration threshold may be set to prevent thermal diffusion effects from causing unwanted damage in tissue surround a treatment zone. The risk of such damage may depend on the region of the patient's body to be treated. The predetermined total duration threshold may therefore be variable depending on the type of treatment. In one example, the predetermined total duration threshold may be equal to or less than 10 seconds. In another example, the predetermined total duration threshold may be equal to or less than 3 seconds.

Alternatively or additionally, the generator may be operable to terminate the second portion when an impedance determined from the detected voltage and current meets or exceeds a predetermined threshold. In other words, the information derived from the plurality of RF pulses can be used to cut short the second portion, e.g. to prevent tissue charring or sticking to the instrument.

The generator may comprises a display arranged to show any one or more of: an impedance determined from the detected voltage and current; a selected power for the microwave electromagnetic energy; an amount of energy delivered from the electrosurgical instrument; information indicative of a state of tissue at the distal end assembly. The information indicative of a state of tissue may be derived from the determined impedance value, and may for example be a simple graphical indicator shows whether or not there is a bleed in the tissue being treated.

The electrosurgical instrument may be an device suitable for delivering RF and microwave energy. For example, the electrosurgical instrument may have a bipolar energy delivery configuration, in which the distal tip assembly comprises a first electrode and a second electrode separated by a dielectric material. The first and second conductive elements may be arranged to act as active and return electrodes to conduct the RF electromagnetic energy through biological tissue located adjacent the distal end assembly, and as a near field antenna to radiate the microwave electromagnetic energy into biological tissue.

The feed cable may be a coaxial cable having an inner conductor separated from an outer conductor by a dielectric material. The inner conductor may be electrically connected to or form part of the first electrode. The outer conductor may be electrically connected to or form part of the second electrode.

The apparatus of the invention may comprise or be used with a surgical scoping device, e.g. an endoscope, gastroscope, laparoscope or the like. The scoping device may have a housing for locating outside a patient's body, and an instrument cord extending from the housing and being insertable into the patient's body to reach a treatment site. The instrument cord may have an instrument channel running therethrough, wherein the electrosurgical instrument and feed cable can be dimensioned to fit within the instrument channel to deliver the RF electromagnetic energy and the microwave electromagnetic energy to the treatment site.

The present invention may be particular advantageous when used in a scoping device environment, especially where a maximum available power of microwave electromagnetic energy at the distal end of the instrument channel is limited either due to losses along the cable. If the maximum available power of microwave electromagnetic energy is equal to or less than 40 W, the composite waveform of the invention can enable more rapid and efficient haemostasis that using microwave energy alone.

The generator described above may be an independent aspect of the invention.

In another aspect of the invention there is provided a method of delivering RF electromagnetic energy and microwave electromagnetic energy from an electrosurgical generator to electrosurgical instrument that has a distal tip assembly for delivering RE electromagnetic energy and microwave electromagnetic energy into biological tissue, the method comprising operating the generator to deliver the RF electromagnetic energy and the microwave electromagnetic energy in a composite waveform for promoting haemostasis in biological tissue, the composite waveform comprising: a first portion comprising primarily RF electromagnetic energy, and a second portion following the first portion, the second portion comprising primarily microwave electromagnetic energy, wherein the second portion further comprises a plurality of RF pulses, wherein the first portion transitions to the second portion when either: a duration of the first portion meets or exceeds a predetermined duration threshold, or an impedance determined by the generator during the first portion meets or exceeds a predetermined impedance threshold.

The method may include any of the operations performed by the generator that are discussed above.

In this specification "microwave" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. In contrast, this specification uses "radiofrequency" or "RF" to indicate a frequency range that is at least three orders of magnitude lower, e.g. up to 300 MHz, preferably 10 kHz to 1 MHz.

The invention may be combined with any or all of the components (either individually or in any combination) described above with reference to the electrosurgical apparatus 400 as set out in GB 2 486 343. For example, the RE channel and microwave channel may include any or all of the components of the RF channel and microwave channel respectively described above.

BRIEF DESCRIPTION OF THE DRAWINGS

Embodiments of the invention are discussed below with reference to the accompanying drawings, in which.

DETAILED DESCRIPTION; FURTHER OPTIONS AND PREFERENCES

Figure 1:
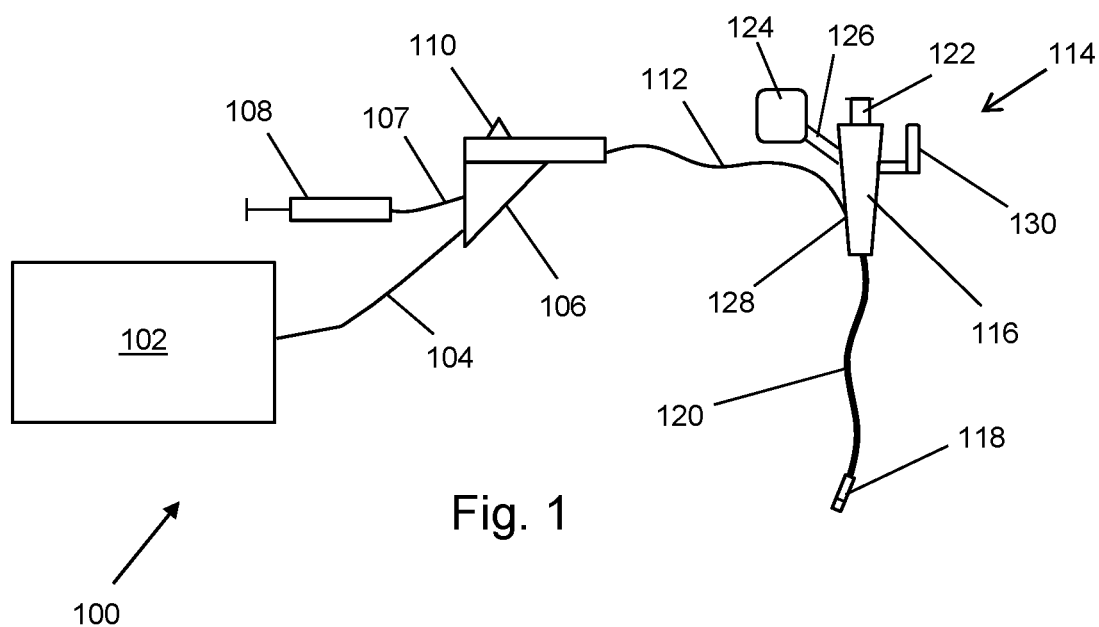
FIG. 1 is a schematic diagram showing an electrosurgery system for use in an embodiment of the invention.
Figure 3:
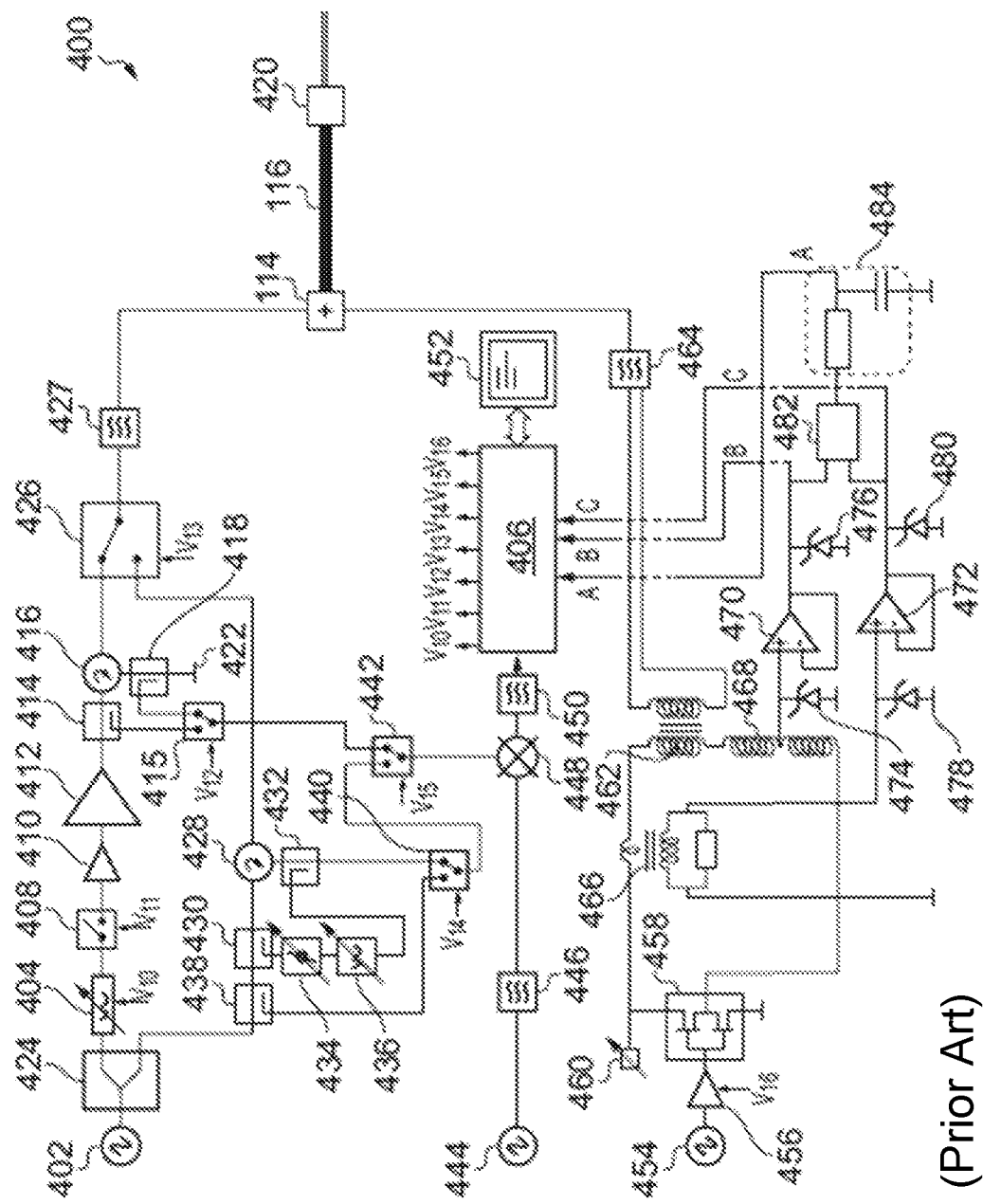
FIG. 3 is an overall schematic system diagram of an electrosurgical apparatus in which the present invention may be used.

FIG. 1 is a schematic diagram of a complete electrosurgery system 100 that is capable of supplying RF energy and microwave energy to the distal end of an electrosurgical instrument. The system 100 comprises a generator 102 for controllably supplying radiofrequency (RF) and microwave energy. The generator 102 may be as shown in the electrosurgical apparatus 400 discussed above with reference to FIG. 3. The generator 102 may be arranged to monitor reflected signals received back from the instrument in order to determine an appropriate signal to be conveyed to the instrument. For example, the generator may be arranged to calculate an impedance seen at the distal end of the instrument in order to determine an optimal delivery power level. This is discussed in more detail below.

The generator 102 is connected to an interface joint 106 by an interface cable 104. The interface joint 106 may also be connected to receive a fluid supply 107 from a fluid delivery device 108, such as a syringe, although this need not be essential. If needed, the interface joint 106 can house an instrument control mechanism that is operable by sliding a trigger 110, e.g. to control longitudinal (back and forth) movement of one or more control wires or push rods (not shown). If there is a plurality of control wires, there may be multiple sliding triggers on the interface joint to provide full control. The function of the interface joint 106 is to combine the inputs from the generator 102, fluid delivery device 108 and instrument control mechanism into a single flexible shaft 112, which extends from the distal end of the interface joint 106.

The flexible shaft 112 is insertable through the entire length of an instrument (working) channel of a surgical scoping device 114, such as an endoscope, gastroscope, laparoscope or the like.

The surgical scoping device 114 comprises a body 116 having a number of input ports and an output port from which an instrument cord 120 extends. The instrument cord 120 comprises an outer jacket which surrounds a plurality of lumens. The plurality of lumens convey various things from the body 116 to a distal end of the instrument cord 120. One of the plurality of lumens is the instrument channel discussed above. Other lumens may include a channel for conveying optical radiation, e.g. to provide illumination at the distal end or to gather images from the distal end. The body 116 may include a eye piece 122 for viewing the distal end. In order to provide illumination at the distal end, a light source 124 (e.g. LED or the like) may be connected to the body 116 by an illumination input port 126.

The flexible shaft 112 has a distal assembly 118 (not drawn to scale in FIG. 1) that is shaped to pass through the instrument channel of the surgical scoping device 114 and protrude (e.g. inside the patient) at the distal end of the bronchoscope's tube. The distal end assembly includes an active tip for delivering radiofrequency and/or microwave energy into biological tissue.

The structure of the distal assembly 118 may be arranged to have a maximum outer diameter equal to or less than 2.0 mm, e.g. less than 1.9 mm (and more preferably less than 1.5 mm) and the length of the flexible shaft can be equal to or greater than 1.2 m.

The body 116 includes a power input port 128 for connecting to the flexible shaft, which comprises a coaxial cable (e.g. a conventional coaxial cable) capable of conveying the radiofrequency and microwave energy from the generator 102 to the distal assembly 118. Coaxial cables that are physically capable of fitting down the instrument channel of a ENB device are available with the following outer diameters: 1.19 mm (0.047"), 1.35 mm (0.053"), 1.40 mm (0.055"), 1.60 mm (0.063"), 1.78 mm (0.070"). Custom-sized coaxial cables (i.e. made to order) may also be used.

It may be desirable to control the position of at least the distal end of the instrument cord 120. The body 116 may include a control actuator 130 that is mechanically coupled to the distal end of the instrument cord 120 by one or more control wires (not shown), which extend through the instrument cord 120. The control wires may travel within the instrument channel or within their own dedicated channels. The control actuator 130 may be a lever or rotatable knob, or any other known catheter manipulation device. The manipulation of the instrument cord 120 may be software-assisted, e.g. using a virtual three-dimensional map assembled from computer tomography (CT) images.

Figure 2:
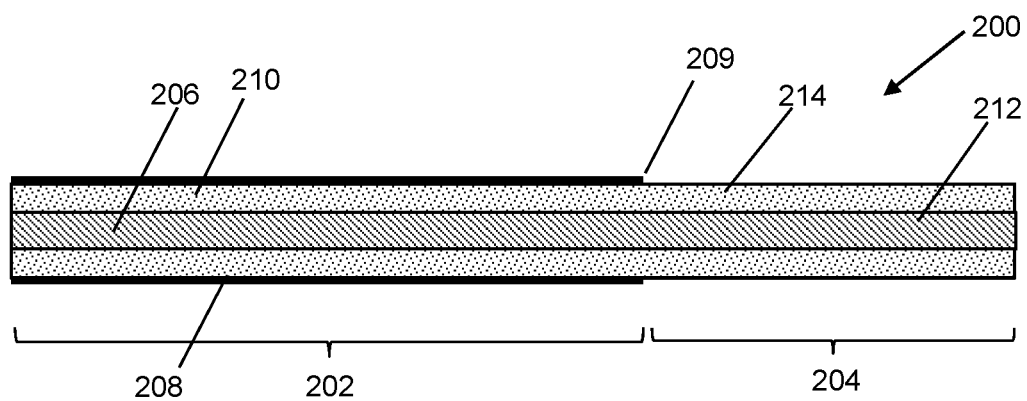
FIG. 2 is a cross-sectional view through an electrosurgical instrument that is suitable for use in the present invention.

FIG. 2 is a cross-sectional view of the distal end of an electrosurgical instrument 200 that can used in the distal assembly 118 to delivery RF energy and microwave energy into biological tissue. The electrosurgical instrument 200 comprises a coaxial cable 202 that is connected at its proximal end to a electrosurgical generator (not shown) in order to convey radiofrequency (RF) and microwave energy. The coaxial cable 202 comprises an inner conductor 206, which is separated from an outer conductor 208 by a first dielectric material 210. The coaxial cable 202 is preferably low loss for microwave energy. A choke (not shown) may be provided on the coaxial cable to inhibit back propagation of microwave energy reflected from the distal end and therefore limit backward heating along the device.

The coaxial cable 202 terminates at its distal end with a radiating tip section 204. In this embodiment, the radiating tip section 204 comprises a distal conductive section 212 of the inner conductor 206 that extends before a distal end 209 of the outer conductor 208. The distal conductive section 212 is surrounded at its distal end by a dielectric tip 214 formed from a second dielectric material, which can be the same or different from the first dielectric material 210. The length of the dielectric tip 214 is shorter than the length of the distal conductive section 212.

The coaxial cable 202 and radiating tip section 204 may have a biocompatible outer sheath (not shown) formed over their outermost surfaces. The outer sheath 218 may be formed from a biocompatible material.

The dielectric tip 214 may have any suitable distal shape, e.g. any of dome shape, cylindrical, conical, etc. A smooth dome shape may be preferred because it increases the mobility of the antenna as it is manoeuvred through small channels.

Figure 4:
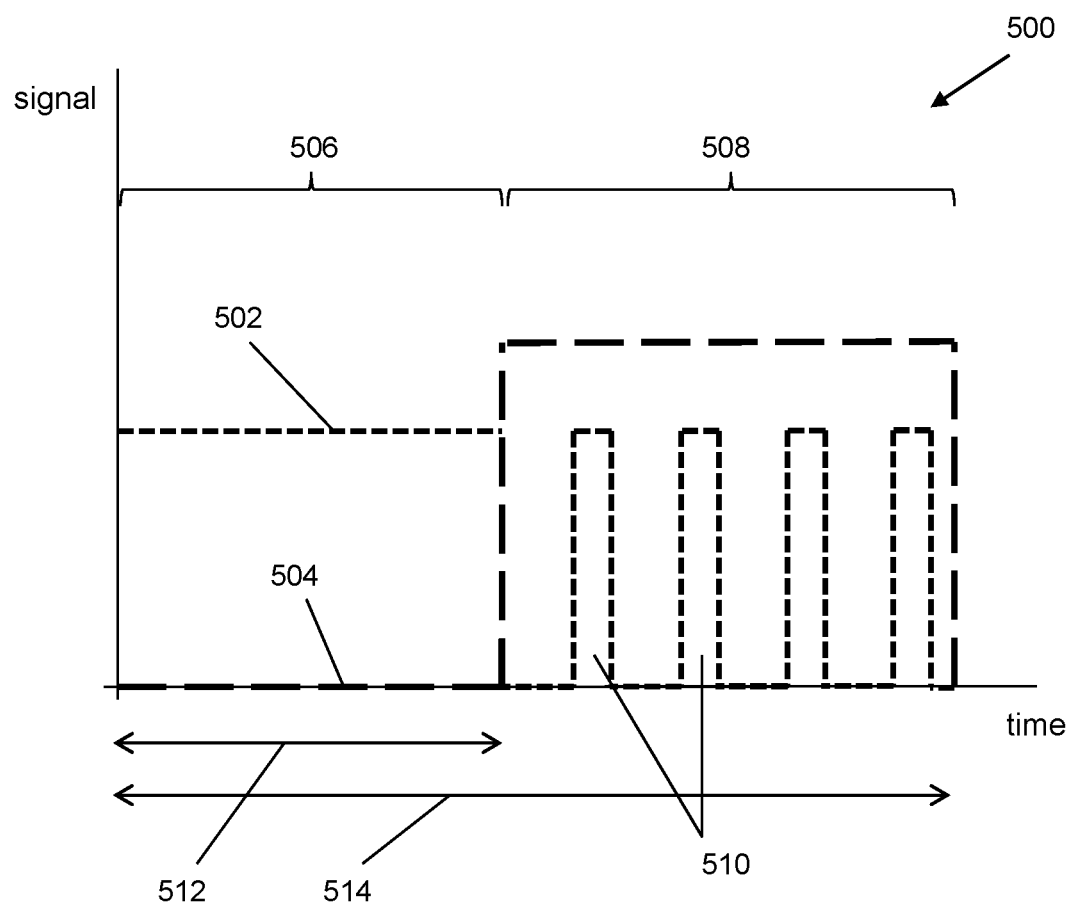
FIG. 4 is a schematic representation of a composite coagulation waveform according to an embodiment of the invention.

FIG. 4 is a schematic representation of a composite coagulation (haemostasis) waveform 500 for delivery from an electrosurgical instrument such as that discussed above in an embodiment of the invention. In FIG. 4, the waveform 500 is depicted as a graph having time along the x-axis and signal strength along the y-axis. The waveform 500 comprises an RF signal 502 and a microwave signal 504 that are supplied separately or simultaneously according to the schema set out below.

The composite waveform 500 of the invention comprises a first portion 506 in which RF energy 502 is delivered either alone or with a level of microwave energy 504 that has a negligible effect on biological tissue. The impedance at the end of the instrument is monitored by detecting the voltage and current associated with the delivered RF energy, e.g. using the detection set up discussed above with reference to FIG. 3.

Following the first portion 506, the composite waveform 500 comprises a second portion 508 in which microwave energy 504 is delivered into the biological tissue. During the second portion, a plurality of short pulses 510 of concurrent RF energy are delivered in a periodic manner. The duration of each pulse 510 is arranged to enable an impedance measurement to be obtained. This impedance measurement can be used to determine a duration for the second portion 508, i.e. to determine when to terminate the waveform 500. Additionally or alternatively, the measured impedance may be used to update a display (not shown) on the generator. The display may show a value for the impedance, or may show a graphical representation of tissue state at the distal end of the instrument, e.g. to provide a straightforward indication of whether or not the tissue is bleeding or not. In another example, the impedance measurement may be used to update a calculation of the amount of energy delivered into tissue, e.g. using known information about the delivered power. The delivered energy does may also be displayed for the operator. The display may be updated periodically, e.g. at one second intervals.

The transition between the first portion 506 and the second portion 508 occurs either when the duration 512 of the first portion 506 reaches or exceeds a predetermined threshold, or when the detected impedance obtained during the first portion 506 reaches or exceeds a predetermined threshold, whichever occurs first. The predetermined threshold for the duration may be equal to or less than one second the predetermined threshold for the tissue impedance may be set to be a certain proportion of the initially measured impedance. For example, the predetermined threshold may be set to be 25% higher than the initial impedance value.

The purpose of the first portion 506 is to enable energy to be delivered as quickly as possible without causing tissue charring. The RF energy 502 in this portion may be a continuous wave signal having an RMS voltage set a level which causes heating to tail off as the tissue impedance rises. For example, the RMS voltage of the RF energy may be set in the range 90 to 120V. The second portion 508 is arranged to switch in after the first portion 506 to maintain the tissue heating (haemostasis) effect without the risk of tissue charring. Even if there has been some local desiccation of tissue during the first portion, the microwave field emitted by the instrument is able to propagate through such desiccated (and therefore non-conductive) tissue so that coagulation performance is not stalled.

The use of microwave frequency energy after the application of RF energy is beneficial because it is possible to achieve a greater depth of direct tissue heating, which is distinct from thermal diffusion effects that may be derived from tissue heated only near the boundary with the instrument.

The frequency of the microwave energy is selected to provide a desired depth of heating. In general, the lower the microwave frequency, the greater the depth of direct heating of biological tissue. Accordingly, if treatment is to be performed in locations where there is a concern not to damage muscle layers located beneath the tissue to be treated, it is desirable to select a microwave frequency (such as 5.8 GHz or higher) in order to limit the energy delivery to a desired region.

For a similar reason, it is desirable to deliver the RF energy from an instrument that has a bipolar electrode configuration, i.e. where the path for the RF energy is localised in the region around the instrument tip. This can avoid a limitation associated with monopolar instruments, in which the electrical pathway between a monopolar electrode tip in contact with tissue and its associated patient return pad will follow a path of least electrical resistance, which in turn can cause significant heating at an (unknown) distance from the point of contact of the instrument with tissue. Indeed, the path of least resistance is typically through the contents of blood vessels which can increase the risk and extent of remote thermal damage.

A further constraint in selecting the frequency for the microwave energy, which is of particular relevance when the instrument is inserted down the instrument channel of a surgical scoping device, is that the higher the microwave frequency, the greater the fractional loss in the energy delivery cable. Loss in the cable causes endoluminal heating, which has to be either constrained or removed to prevent unwanted collateral damage along the length of the cable. Removing the endoluminal heating may require a circulating coolant, which requires a more complicated delivery structure in what is already a confined working environment. Constraining the cable loss inevitably means that less power is available at the distal end of the instrument. This can mean that more time is needed to deliver the overall required amount of heat energy, which can be undesirable because the longer the treatment period, the larger the effects of thermal diffusion, which can cause damage to surrounding musculature, and perfusion cooling, where blood flow acts to draw the heat energy away from the local treatment site.

The waveform 500 represents a balance between the factors outlined above. The first portion 506 delivers RF energy at a point when the biological tissue is most receptive to it (without causing charring or other unwanted thermal damage), while the second portion 508 can continue the haemostasis effect that is initiated by the RF energy in the first portion 506 in order to deliver a total heat energy amount within a desired duration.

It is preferable for the duration 514 of the waveform 500 to be equal to or less than ten seconds in order to control the zone of tissue damage resultant from thermal diffusion. However, the actual duration that is acceptable may vary depending on the location of the treatment region. For example, treatment in the lower gastrointestinal tract may need to have a shorter overall treatment time, e.g. equal to or less than three seconds in order to avoid damage to the surrounding musculature. On the other hand, if the bleed to be coagulated is in tissue that is not closely coupled to the wall of the gastrointestinal tract, e.g. in the case of a pedunculated polyp, then the coagulation waveform 500 may be applied repeatedly without causing unwanted damage. During the second portion 508, the microwave energy may be supplied as a continuous wave signal having a pre-set (e.g. user defined) power level.

The invention claimed is:

1. An electrosurgical apparatus comprising:
   an electrosurgical generator arranged to generate radiofrequency (RF) electromagnetic energy and a microwave electromagnetic energy;
   a bipolar electrosurgical instrument having a distal tip assembly for delivering RF electromagnetic energy and microwave electromagnetic energy into biological tissue; and
   a feed cable connected to deliver the RF electromagnetic energy and the microwave electromagnetic energy from the electrosurgical generator to the bipolar electrosurgical instrument,
   wherein the electrosurgical generator is arranged to detect a voltage and a current associated with the delivered RF electromagnetic energy, and
   wherein the generator is operable to:
      determine an impedance from the detected voltage and current;
      deliver the RF electromagnetic energy and the microwave electromagnetic energy in a composite waveform for promoting haemostasis in biological tissue, the composite waveform comprising:
         a first portion comprising primarily RF electromagnetic energy, and
         a second portion following the first portion, the second portion comprising primarily microwave electromagnetic energy,
   wherein the second portion further comprises a plurality of RF pulses,
   wherein the generator is arranged to:
      determine an impedance from the detected voltage and current during the first portion; and
      cause the composite waveform to transition from the first portion to the second portion when either:
         a duration of the first portion meets or exceeds a predetermined duration threshold, or
         the impedance determined during the first portion meets or exceeds a predetermined impedance threshold.

2. An electrosurgical apparatus according to claim 1, wherein the predetermined duration threshold is equal to or less than 1 second.

3. An electrosurgical apparatus according to claim 1, wherein the electrosurgical generator is arranged to determine an initial impedance from the detected voltage and current associated with the RF electromagnetic energy delivered at the beginning of the first portion, and wherein the predetermined impedance threshold is a preset proportion of the initial impedance.

4. An electrosurgical apparatus according to claim 3, wherein the preset proportion is equal to or more than 1.25.

5. An electrosurgical apparatus according to claim 1, wherein the generator is arranged to deliver the RF electromagnetic energy as a continuous wave signal in the first portion.

6. An electrosurgical apparatus according to claim 5, wherein the continuous wave signal of RF electromagnetic energy has a RMS voltage in the range 90-120 V.

7. An electrosurgical apparatus according to claim 1, wherein the generator is arranged to prevent delivery of microwave electromagnetic energy in the first portion.

8. An electrosurgical apparatus according to claim 1, wherein the generator is arranged to deliver the microwave energy as a continuous wave in the second portion.

9. An electrosurgical apparatus according to claim 1, wherein the generator is arranged to determine an impedance value from detected voltages and currents associated with each of the plurality of RF pulses delivered during the second portion.

10. An electrosurgical apparatus according to claim 9, wherein the generator is arranged to calculate an amount of heat energy delivered by the bipolar electrosurgical instrument based on the determined impedance values.

11. An electrosurgical apparatus according to claim 1, wherein the generator is arranged to supply the plurality of RF pulses concurrently with the microwave electromagnetic energy.

12. An electrosurgical apparatus according to claim 1, wherein the generator is arranged to supply the plurality of RF pulses in a periodic manner.

13. An electrosurgical apparatus according to claim 1, wherein each of the plurality of RF pulses is arranged to have a negligible thermal effect on the biological tissue.

14. An electrosurgical apparatus according to claim 1, wherein the generator is operable to:
   determine an amount of heat energy delivered by the bipolar electrosurgical instrument; and
   terminate the second portion when either:
      the amount of heat energy determined by the generator meets or exceeds a predetermined heat energy threshold, or
      a duration of the composite waveform meets or exceeds a predetermined total duration threshold.

15. An electrosurgical apparatus according to claim 14, wherein the predetermined total duration threshold is equal to or less than 10 seconds.

16. An electrosurgical apparatus according to claim 14, wherein the predetermined total duration threshold is equal to or less than 3 seconds.

17. An electrosurgical apparatus according to claim 1, wherein the generator is operable to:
   determine an impedance from the detected voltage and current associated with one of the plurality of RF pulses; and
   terminate the second portion when the determined impedance meets or exceeds a predetermined threshold.

18. An electrosurgical apparatus according to claim 1, wherein the generator comprises a display arranged to show any one or more of:
   the impedance determined from the detected voltage and current;
   a selected power for the microwave electromagnetic energy;
   an amount of energy delivered from the bipolar electrosurgical instrument;
   information indicative of a state of tissue at the distal end assembly.

19. An electrosurgical apparatus according to claim 1, wherein the distal tip assembly comprises a first electrode and a second electrode separated by a dielectric material.

20. An electrosurgical apparatus according to claim 19, wherein the first and second conductive elements are arranged to act:
   as active and return electrodes to conduct the RF electromagnetic energy through biological tissue located adjacent the distal end assembly, and
   as a near field antenna to radiate the microwave electromagnetic energy into biological tissue.

21. An electrosurgical apparatus according to claim 1 comprising a surgical scoping device having an instrument cord for insertion into a patient's body to reach a treatment site, the instrument cord having an instrument channel running therethrough, wherein the bipolar electrosurgical instrument and feed cable are dimensioned to fit within the instrument channel to deliver the RF electromagnetic energy and the microwave electromagnetic energy to the treatment site.

22. An electrosurgical apparatus according to claim 21, wherein a maximum available power of microwave electromagnetic energy at the distal end of the instrument channel is equal to or less than 40 W.

23. A method of delivering RF electromagnetic energy and microwave electromagnetic energy from an electrosurgical generator to a bipolar electrosurgical instrument that has a distal tip assembly for delivering RF electromagnetic energy and microwave electromagnetic energy into biological tissue, the method comprising operating the generator to deliver the RF electromagnetic energy and the microwave electromagnetic energy in a composite waveform for promoting haemostasis in biological tissue, the composite waveform comprising:
   a first portion comprising primarily RF electromagnetic energy, and
   a second portion following the first portion, the second portion comprising primarily microwave electromagnetic energy,
   wherein the second portion further comprises a plurality of RF pulses,
   wherein the first portion transitions to the second portion when either:
      a duration of the first portion meets or exceeds a predetermined duration threshold, or
      an impedance determined by the generator during the first portion meets or exceeds a predetermined impedance threshold.

24. A method according to claim 23 including determining the impedance from a detected voltage and current of the RF electromagnetic energy.

25. A method according to claim 24 including determining an initial impedance from the detected voltage and current associated with the RF electromagnetic energy delivered at the beginning of the first portion, and wherein the predetermined impedance threshold is a preset proportion of the initial impedance.

26. A method according to claim 23 including determining an impedance value from detected voltages and currents associated with each of the plurality of RF pulses delivered during the second portion.

27. A method according to claim 26 including calculating an amount of heat energy delivered by the bipolar electrosurgical instrument based on the determined impedance values.

28. A method according to claim 23 including terminating the second portion when either:
   an amount of heat energy delivered by the bipolar electrosurgical instrument meets or exceeds a predetermined heat energy threshold, or
   a duration of the composite waveform meets or exceeds a predetermined total duration threshold.

* * * * *